United States Patent [19]

Rader

[11] 4,289,023
[45] Sep. 15, 1981

[54] PERCUSSION METHOD AND APPARATUS FOR THE INVESTIGATION OF A CASING CEMENT IN A BOREHOLE

[75] Inventor: Dennis Rader, Houston, Tex.

[73] Assignee: Schlumberger Technology Corp., New York, N.Y.

[21] Appl. No.: 76,834

[22] Filed: Sep. 19, 1979

[51] Int. Cl.³ ............................................. E21B 47/00
[52] U.S. Cl. ......................................... 73/151; 73/12; 73/588
[58] Field of Search .............. 73/12, 151, 152, 150 A, 73/588; 166/253; 181/105; 367/35

[56] References Cited

U.S. PATENT DOCUMENTS

| | | | |
|---|---|---|---|
| 2,412,240 | 12/1946 | Williams et al. | 73/588 X |
| 2,641,927 | 6/1953 | Grable et al. | 73/151 |
| 2,672,050 | 3/1954 | Sewell | 73/151 |
| 3,759,085 | 9/1973 | Wilson et al. | 73/12 |
| 3,879,982 | 4/1975 | Schmidt | 73/12 |

FOREIGN PATENT DOCUMENTS 194694 6/1967 U.S.S.R.

*Primary Examiner*—Jerry W. Myracle
*Attorney, Agent, or Firm*—William R. Sherman; Kenneth Olsen; Louis H. Reens

[57] ABSTRACT

A percussion technique is described with which an impulse is applied to an element to bounce it off the inner surface of a casing cemented in a borehole. The movement of the element is automatically measured to produce information from which the bond between the casing and cement behind the point of impact of the element can be evaluated. In accordance with one embodiment, the cement bond evaluation is automatically derived by comparing impact and rebound velocities of the element such as by generating a coefficient of restitution of the bouncing element. In another embodiment, the contact time of the element with the casing is measured to derive an indication of the quality of the cement bond.

19 Claims, 4 Drawing Figures ically spaced zones may occur. Various acoustic techniques have been described to evaluate the quality of the cement bond. Such techniques may employ an ultrasonic source which is particularly effective in a casing containing water or a mixture of water and mud. In a dry casing, however, a sonic source is not practical for evaluation of the casing-cement interface.

PERCUSSION METHOD AND APPARATUS FOR THE INVESTIGATION OF A CASING CEMENT IN A BOREHOLE

FIELD OF THE INVENTION

This invention relates to a technique for evaluating the cement bond between the casing and cement in a borehole in an earth formation. More specifically, this invention relates to a percussion method and apparatus for evaluating the casing cement bond.

BACKGROUND OF THE INVENTION

In the exploration for oil, it is a common technique to set casings into a borehole and introduce cement around the casing. The cement hydraulically isolates vertically separated zones to thus avoid contamination of a hydrocarbon bearing zone. It is particularly important to confirm that the cement is hydraulically secure without spaces between the casing and the cement through which hydraulic communication between vertically spaced zones may occur. Various acoustic techniques have been described to evaluate the quality of the cement bond. Such techniques may employ an ultrasonic source which is particularly effective in a casing containing water or a mixture of water and mud. In a dry casing, however, a sonic source is not practical for evaluation of the casing-cement interface.

Percussion techniques to evaluate the cement bond behind a casing have been described such as in Russian Patent Publication No. 194,694 of June 16, 1967. In U.S. Pat. No. 2,641,927 to Grable et al a percussion of the well pipe introduces vibrations which are monitored at a remote location to derive an evaluation of the cement bond. In U.S. Pat. No. 2,672,050 to Sewell a technique is described for measuring the deformability of a well casing to detect poorly bonded regions.

In an experimental technique known to the inventor hereof, a steel ball is dropped against a plate to introduce plate vibrations, which, with the measurement of the force of impact of the ball, provides an indication of the character of the cement bond behind the plate. As part of the experiment, the duration of contact of the ball with the plate and the velocity of the ball are measured. The duration of contact was found to be barely affected by the thickness of the plate or whether there exists a good or poor cement bond below the impact point on the plate. A device for measuring the rate of deceleration of a rigid body as it is impacted on material is described in U.S. Pat. No. 3,759,085 to Wilson et al.

The reliance upon the remote detection of percussion generated vibrations in a casing to evaluate the cement bond as described in the above art either yields an undesirably coarse evaluation, as in the Grable et al technique or involves complex devices which make the evaluation difficult to implement.

SUMMARY OF THE INVENTION

In a percussion technique for evaluating the cement bond behind a casing in accordance with the invention, an element is located to impact on an inner casing surface. An impulse is applied to the element to move it towards and bounce it off the casing. The impulse is sufficiently short in duration to enable the element to move freely prior to impact. The motion of the element is sensed to enable an evaluation of the cement bond behind the impact point on the casing. In one embodiment, the motion just prior to and after impact is sensed. In another embodiment, contact time is measured and used.

As described with reference to one technique for determining the quality of the cement bond, the velocity of the element is measured just before and after impact with the casing. A comparison between impact and rebound velocities is then formed as a characterization of the quality of the cement bond. For example, if the comparison is a ratio formed by dividing the measured rebound velocity by the measured impact velocity, then a low ratio value is indicative of a poor cement bond and a high ratio value indicates a good bond.

A percussion technique for evaluating the cement bond in accordance with the invention advantageously permits an evaluation of the cement bond in a small region behind the casing. This technique may be used in an empty casing which is free of water or mud. Bonded and unbonded local cement-bond conditions can be distinguished.

Since no acoustic coupling is required, the energy imparted by the element to the casing is transmitted to the cement behind the casing with a portion of energy reflected at this interface to influence the motion of the element in a manner which is distinctly different from the case in which cement is locally absent. In the presence of bonded cement relatively little energy is reflected at the casing-cement interface thereby inhibiting vibratory motion of the casing. This leads to a relatively high rebound energy of the element and thus a high coefficient of restitution. The associated contact time is relatively low in this case as well. In the absence of bonded cement, the rebound energy and coefficient of restitution are lower while the contact time is relatively long. Even in the presence of small microfractures, which are sufficiently small to be hydraulically secure cement-casing interfaces, the presence of the cement can be detected from the return energy of the element.

As described herewith with reference to one percussion technique for the evaluation of the casing cement-bond, an element is mounted inside the casing and reciprocated to provide a motion signal representative of the motion of the element. In one form, the velocity of the element just prior to and after impact with the casing is measured from the motion signal.

The measurement of the element velocity or contact time may be done utilizing analog or digital devices. A record of the ratio between impact and rebound velocities of the element the amount of time it remains in contact with the casing can be made to enable logging of the casing-cement bond with circumferential resolution over extended casing lengths.

It is, therefore, an object of the invention to provide a method and apparatus for determining the quality of the cement bond behind a casing utilizing a percussion technique. It is a further object of the invention to provide a method and apparatus for evaluating, with circumferential resolution, the cement bond behind an empty casing in which there is no liquid in the casing regions being investigated. These and other objects and advantages of the invention can be understood from the following detailed description of an embodiment which is described in conjunction with the drawings.

DETAILED DESCRIPTION OF EMBODIMENT

Figure 1:
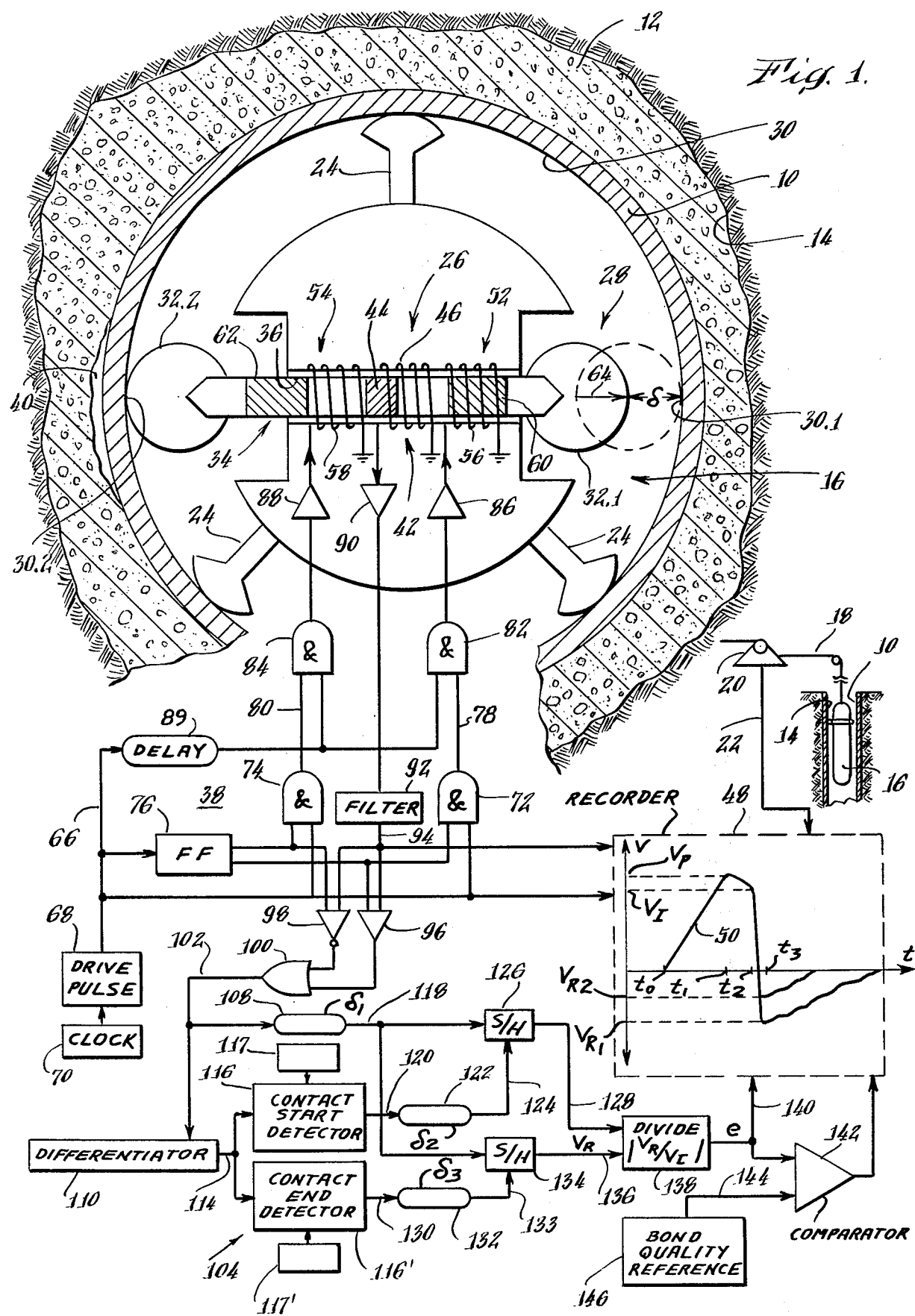
FIG. 1 is a schematic representation of an apparatus in accordance with the invention for determining the quality of the cement bond behind a casing using a percussion technique.
Figure 2:
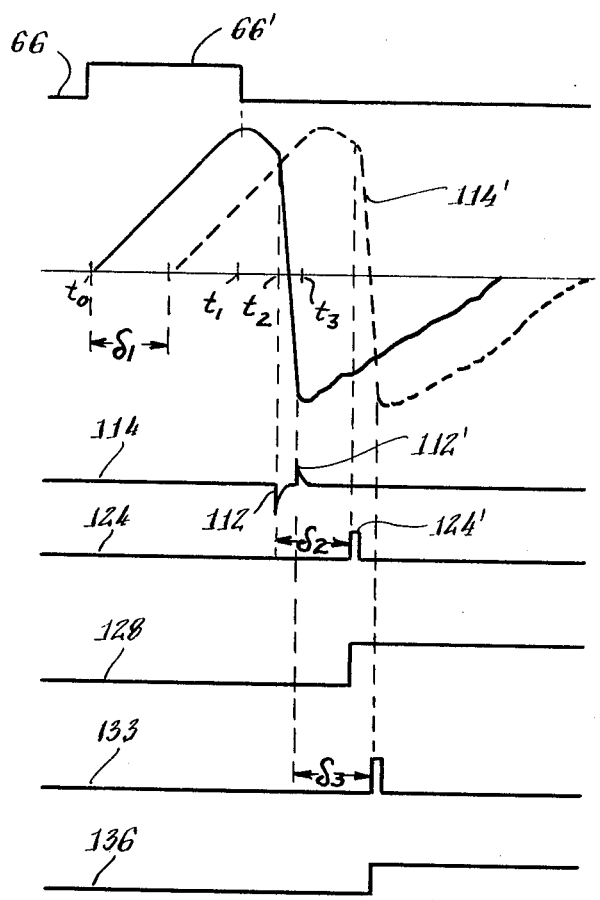
FIG. 2 is a timing diagram for certain waveforms generated within the apparatus of FIG. 1.

With reference to FIGS. 1 and 2, a well casing 10 is shown cemented with an annular cement zone 12 within a borehole 14 in an earth formation. A tool 16 is suspended inside the casing from a cable 18 through which electrical power and suitable control signals can be transmitted. The cable 18 is coupled to a depth measuring device 20 from which an indication of the depth position of tool 16 is produced on a line 22.

Tool 16 is shown provided with centralizers such as 24 to maintain the tool in the center of casing 10. A percusssion apparatus 26 is mounted in tool 16 to explore the casing 10 by bouncing an element such as 28 off the inner surface 30 of casing 10. Additional percussion apparatuses may be used, one being shown here for illustration.

In the embodiment of FIG. 1 the element 28 is mounted to reciprocate along a diameter of cylindrical casing 10 to impact on diametrically opposite casing surface segments 30.1 and 30.2 of casing 10. The element 28 is formed with a pair of hardened steel balls 32 connected by a rigid shank 34.

Element 28 is slidably mounted in a smooth-fitting bore 36 of tool 16 with low friction to reduce drag produced by the mounting arrangement for element 28 as it is driven towards casing 10.

The element 28 is driven towards casing 10 with an impulse generator 38 which produces impulses needed to impact element 28 onto casing 10. These impulses are of sufficiently short duration so that the impulses terminate before the element 28 makes contact with the inner surface 30. As a result, the motion of element 28 after the impulse is substantially free from external influences other than the effect of fluid inside casing 10.

When element 28 freely advances towards casing 10 after termination of an impulse, a localized cement evaluation can be made by measuring the velocity of the element just prior to and just after impact with casing 10. A comparison of these velocity measurements, i.e. the impact and rebound velocities respectively, enables one to characterize the quality of the cement bond behind the casing.

For example, when element 28 is driven against segment 30.1 of casing 10, the presence of a cement bond improves the elastic behavior of casing segment 30.1, thus enabling element 28 to bounce back at a rebound velocity which more closely approximates the impact velocity.

On the other hand, when element 28 is impacted against segment 30.2 of casing 10, the presence of a poor cement bond, such as a void 40, degrades elastic behavior of segment 30.2 and correspondingly reduces the rebound velocity of the element 28.

A motion sensor 42 is employed with element 28 to provide a motion signal representative of the motion of the element 28. The motion sensor 42 may be any suitable device such as an accelerometer directly mounted on element 28, or as in the embodiment of FIG. 1, a magnetic device composed of a permanent magnet 44 and sensor coil 46.

The velocity profile for element 28 may be visually presented on a recorder 48 with a curve 50 showing velocity amplitude as a function of time of the motion signal from sensor 42. At a time to a driving impulse from impulse generator 38 is produced for a time lasting until time $t_1$. The impulse increases the velocity of element 28 to a peak value $V_p$ at $t_1$. From time $t_1$ the element 28 moves freely, losing some speed until at time $t_2$ element 28 makes contact with the inner casing surface 30. At time $t_2$, element 28 has a velocity, $V_I$, representative of the impact velocity of element 28. Following time $t_2$, element 28 reverses its direction of motion and rebounds with an initial peak rebound velocity, $V_R$, occurring at a time $t_3$ generally just after contact with inner casing surface 30 has ceased. The rebound velocity of element 28 then decays towards zero. The peak value, $V_R$, of the rebound velocity is found dependent upon the character of the cement bond between the casing-cement interface behind the point of impact. If there exists a good bond, the peak rebound velocity, $V_R$, at time $t_3$ is higher, $V_{R1}$, in comparison with the peak rebound velocity $V_{R2}$ occurring with a bad bond.

With a method and apparatus in accordance with the invention, the impact velocity, $V_I$, and peak rebound velocity, $V_R$, are automatically measured. These velocity measurements can then be used to derive an evaluation of the character of the cement bond behind the inner casing surface segment upon which the element 28 has impacted.

Where $V_I$ is more or less constant for a given condition, only $V_R$ need be measured. However, since $V_I$ may vary with tool condition, temperature, casing diameter and casing fluid drag, it is preferred to use $V_R$ in comparison with $V_I$.

The cement bond evaluation can be made comparing the measured velocities to, for example, generate a coefficient of restitution or a difference between them. A high value for the coefficient can be recognized as representative of a good cement bond and a low value as a poor cement bond.

The precise boundary between comparison values indicative of a good bond and a bad bond may vary depending upon factors such as plastic deformation of the casing at point of impact, the thickness of the casing wall relative to the mass and contact area of the impact element, surface roughness of inner surface 30, the presence of liquid inside casing 10, and the occurrence of a minute clearance between the casing 10 and cement 12 known as a micro annulus. Such micro annulus may be hydraulically secure if sufficiently small.

By accumulating a sufficient experience of experimental investigations, one may assign a boundary value for a given casing thickness on one side of which the measured comparison represents a good cement bond and on the other side of which a bad bond is measured. In the case of a comparison made to generate a coefficient of restitution ($V_R/V_I$), a bad bond may be detected whenever the coefficient of restitution drops below a boundary value.

In the embodiment of FIG. 1 the impulse generator 38 is in the form of a pair of solenoids 52, 54 composed of drive coils 56, 58 and magnetically sensitive armature segments 60, 62 incorporated with shank 34. Solenoid 52 generates an impulse to drive steel ball 32.1 of element 28 in a direction indicated by arrow 64 against segment 30.1 of inner casing surface 30 and solenoid 54 provides an impulse to drive steel ball 32.2 of element 28 in an opposite direction against segment 30.2 of inner casing surface 30.

Solenoids 52, 54 are alternately actuated by drive pulses such as 66' shown in FIG. 2 and originating on a line 66 from impulse generator 38 periodically actuated by a clock 70. The pulses on line 66 are applied to a pair of AND gates 72, 74 which are alternately enabled by outputs 75.1 and 75.2 from a flip-flop 76 which, in turn, is toggled between its stable states by the pulses on line 66.

The outputs 78, 80 from AND gates 72, 74 are respectively coupled through gates 82, 84, amplifiers 86, 88 to drive coils 56, 58. A delay 89 is used in line 66 so that AND gates 82, 84 are enabled after signals on lines 78, 80 have stabilized following toggling of flip-flop 76.

The duration, $t_0$ to $t_1$, of drive pulses 66' is selected sufficiently long to generate an impulse against element 28 to drive it towards casing 10, yet sufficiently short to terminate the impulse before element 28 makes contact with casing 10. This duration depends upon factors including the mass of the element 28, the effectiveness of the solenoids 52, 54, the free space, S, between element 28 and casing 10, and a maximum limit on the impact velocity of the element to reduce plastic deformation effects at the point of impact.

As a drive pulse 66' is applied to, for example, drive coil 56, motion sensor 42 generates a motion signal caused by the motion of magnetic segment 44 past pickup coil 46. The motion signal is amplified in amplifier 90 and passed through a low pass filter 92 to remove high frequency noise. The motion signal on the output 94 of filter 92 is applied to recorder 48 together, if needed for synchronization, with the drive pulses on line 66 to produce a motion curve such as 50.

The motion signal on line 94 is also applied to a pair of analog logic amplifiers 96, 98 which are alternately enabled by lines 75.1 and 75.2 from flip-flop 76. Amplifier 98 inverts the motion signal, thus presenting a motion signal of like polarity as from amplifier 96 when the motion of magnet 44 is reversed, i.e. in a direction towards inner casing segment 30.2, in response to a drive pulse applied to drive coil 58.

The outputs of amplifiers 96, 98 are combined by analog logic OR gate 100 to apply a common motion signal on line 102 to a motion measuring network 104. The latter provides a measurement of the value of the impact velocity, $V_I$, and rebound velocity, $V_R$, or in the alternative, the contact time.

The impact velocity, $V_I$, is measured by selecting a value of the motion signal on line 102 at a time just prior to $t_2$. This is done by measuring $V_I$ at a time with respect to a precisely measurable event such as a rapid change in the motion of element 28. In the embodiment illustrated in FIG. 1, the impact velocity is measured a predetermined interval prior to sensing of the rapid change in the waveform 50 following contact of element 28 with casing 10. The interval should be of sufficiently long duration to assure sampling of the motion signal on line 102 while the element 28 is in free motion, yet the interval should not be so long as to sample the motion signal while the element 28 is being driven.

The velocity measurements in network 104 are made by applying the motion signal on line 102 to a delay network 108 and a differentiator 110. The latter produces output pulses 112-112' on line 114 when the motion signal undergoes rapid changes such as upon casing contact and a reversal of motion of element 28. Pulse detectors 116-116' are coupled to line 114 to respectively sense the start and end of contact between element 28 and casing 10 by detecting pulses 112-112'. The outputs of pulse detectors 116-116' are short duration pulses occurring near respectively the start and ending of contact between element 28 and casing 10. The pulse detectors 116-116' are polarity and amplitude sensitive so that they can, for example, with the aid of diodes, distinguish between pulses 112-112'.

Amplitude sensitivity is obtained by applying reference levels from sources 117-117'. The latter thus effectively enable the pulse detectors 116 to respond only to large or rapid changes of the motion signal on line 102. Hence, reference source 117 provides a deceleration reference which the motion signal must exceed to produce a pulse on line 125. Similarly, reference source 117' provides a reference level, representative of the speed of motion reversal of element 28, and which the motion signal on line 102 must exceed to produce an output pulse on line 130.

The delay network 108 provides a motion signal on output 118 with a known delay $\delta_1$ sufficient to enable one to sample the impact velocity value after detection of the contact start pulse 112 by pulse detector 116. Typically, a delay $\delta_1$ of the order of about one hundred microseconds can be sufficient, since the interval between the actual start of contact at time $t_2$ and occurrence of pulse 112 is normally less than that.

The pulse on output line 120 is applied to a delay network 122 which produces on line 124 a delayed pulse 124' occurring at a time period $\delta_2$ after pulse 112, where $\delta_2$ is equal to slightly less than the difference between delay $\delta_1$ and the estimated interval between $t_2$ and the pulse 112. The amount by which $\delta_2$ is less than this difference is normally constant and can be experimentally determined. The leading edge of the output pulse on line 124 of delay network 122 actuates a sample and hold network 126 which provides a signal representative of the impact velocity, $V_I$, on output line 128.

The rebound velocity, $V_R$, is measured by applying the pulse output on line 130 of pulse detector 116' through a delay network to provide on line 133 an activating pulse 135 to sample and hold network 134. The network 132 generates a delay $\delta_3$ which may be equal to or slightly larger than the delay $\delta_1$ caused by network 108. The sample and hold network 134 is connected to sample the delayed motion signal on line 118 so that output line 136 carries a signal representative of the rebound velocity $V_R$ of element 28.

An evaluation of the cement bond can be formed after recording the automatically determined impact and rebound velocity measurements on recorder 48. However, such evaluation can be aided by forming a comparison value such as the coefficient of restitution $e = V_R/V_I$ between absolute values of $V_R$ and $V_I$ in a divider network 138. The divider output on line 140 can be recorded on recorder 48. A further step in the cement evaluation can be made by applying the value of the coefficient of restitution to a comparator 142 for comparison with a signal on line 144 representative of the boundary between good and bad cement bonds as produced by an adjustable source 146. The output 148 of the comparator 142 may then be recorded.

Figure 3:
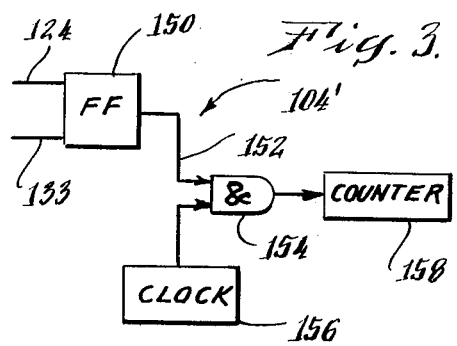
FIG. 3 is a partial schematic representation of an apparatus for measuring contact time of an element impacted on an inner casing surface for determining the quality of the cement bond behind a casing.

A motion measurement can be made by measuring contact time with the output pulses from pulse detectors in a network 104' as shown in FIG. 3. The contact start and end pulses on lines 124, 133 are applied to respectively set and reset inputs of a flip-flop 150. Output 152 of flip-flop 150 controls a gate 154 to which pulses from a clock 156 are also applied. A counter 158 counts the pulses passed through gate 154 to produce a contact signal in the form of a pulse count indicative of the time element 28 is in contact with casing 10. The contact signal may be stored in recorder 48 or in another suitable storage device.

Figure 4:
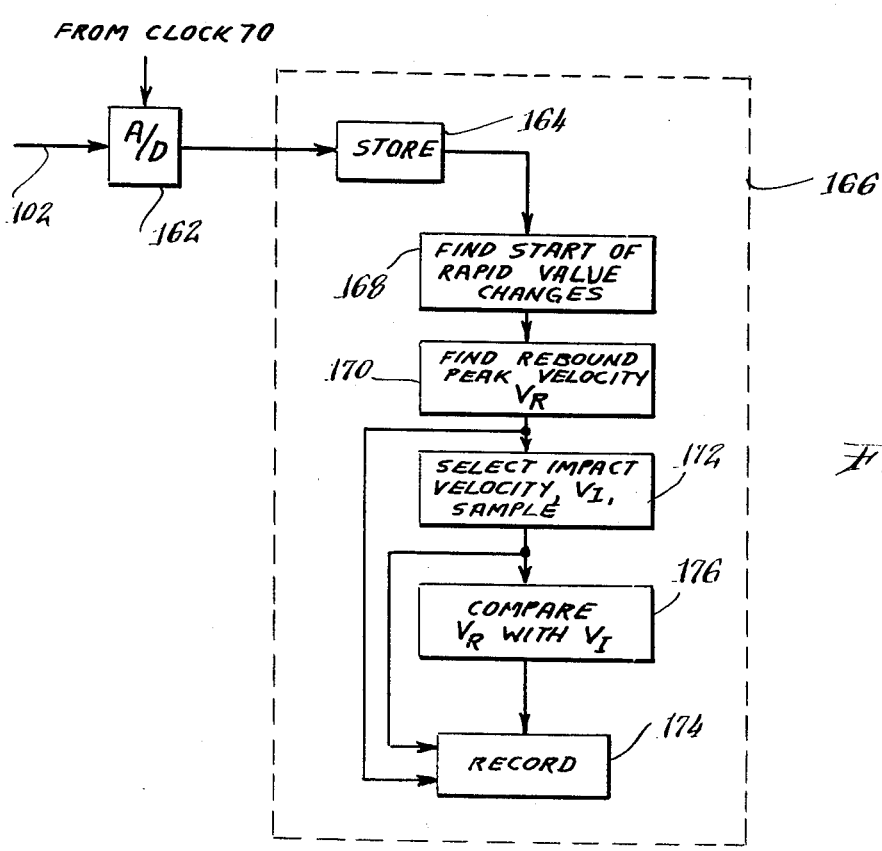
FIG. 4 is a schematic representation of an apparatus in accordance with the invention for deriving with digital techniques the element velocities produced during a percussion investigation of the casing.

With the apparatus described with reference to FIG. 1, cement bond evaluations of cemented casings can be advantageously made. The apparatus can be modified in various ways. For example, element 28 can be formed with a single impacting ball 32 instead of a pair. Such single impacting end can be advantageous in that impulse generating solenoid 54 may be used to return element 28 to a fixed position prior to the application of an impulse from solenoid 52. However, with a bar-bell like arrangement as shown, this would not be necessary. The impulse generator is shown as electromagnetic; however, other devices can be used to apply impulses to element 28, such as a fast acting mechanical hammer. The motion measuring device 104 may also be varied, such as by utilizing a digital apparatus 160 as illustrated in FIG. 4. The motion signal on line 102 is shown therein supplied to an analog to digital (A/D) converter 162 energized by a pulse from clock 70. The A/D converter 162 generates a plurality of digitized samples of the motion signal and these samples are stored in a suitable storage device 164 such as a memory of a microprocessor 166. The stored motion signal samples are then scanned at 168 to determine the place where a rapid change in sample values begins to occur as the starting time of contact. The sample value at a predetermined number of samples prior to the detected starting time sample may then preferably be used as the impact velocity $V_I$ for element 28. The end of contact can be detected at 170, by scanning for the negative peak value as the rebound velocity $V_R$.

A sample which occurs close to the negative peak value is selected or identified at 172 on the basis of the best estimate of the end of contact of element 28 with casing 10. The time difference between the samples representative of start and end of contact then represents the contact time of element 28 with casing 10.

The sample values for $V_I$ and $V_R$ may be recorded at 174 such as by visual presentation or by their storage in memory, or both. A comparison can be performed at 176 such as by forming the difference $V_I - V_R$, or ratio $V_R/V_I$ and the comparison recorded.

Having thus described one percussion technique in accordance with the invention, variations therefrom can be realized. For example, a plurality of elements 28 may be employed on tool 16 to explore circumferentially different segments of a casing. It will thus be evident to persons skilled in the art that the present invention may be carried out in various ways other than those hereinabove described or illustrated in the drawings without departing from the substance of the invention, which is intended to be defined by the appended claims.

What is claimed is:

1. A method for evaluating the cement bond behind a casing cemented in a borehole, comprising the steps of applying an impulse to an element disposed to impact on a segment of an inner surface of the casing to bounce the element off said surface, said impulse terminating prior to contact of the element with the inner casing surface so that said element is moving freely prior to contact with the casing; and measuring the motion of the element for a time period including the element's motion prior to and after the bouncing of said element off said inner wall to enable measurement of the rebound of said element by said casing.

2. The method for evaluating the cement bond as claimed in claim 1 wherein the motion measuring step includes the step of detecting when the deceleration of the element exceeds a predetermined value as the start of contact between the element and the casing;

detecting the reversal of motion of the element as the end of said contact; and measuring the time therebetween as the contact time of the element with said casing.

3. The method for evaluating the cement bond as claimed in claim 1 and further including the steps of measuring the impact and rebound velocities of the element respectively occurring just prior to and after said element bouncing off the inner casing surface.

4. The method for evaluating the cement bond as claimed in claim 3 and further including the step of comparing said measured impact and rebound velocities to form an evaluation of the quality of the casing-cement bond behind the impact segment on the casing.

5. The method for evaluating the cement bond as claimed in claim 4 wherein said comparing step comprises forming a ratio between said impact and rebound velocities to form a coefficient of restitution for the element motion.

6. The method for evaluating the cement bond as set forth in claim 3 wherein said motion measuring step further includes the steps of generating a motion signal representative of the motion and direction of motion of the element; and deriving from said motion signal, impact and rebound signals respectively representative of the impact and rebound velocities of the element just prior to and after impact with said segment of the inner casing surface.

7. The method for evaluating the cement bond as set forth in claim 6 wherein said step to derive the impact signal further includes the steps of determining when the motion signal represents a deceleration of the element in excess of a predetermined amount as the time of impact of the element with the inner casing surface; and selecting as the impact signal a value of the motion signal occurring a predetermined interval prior to the time of said determined deceleration.

8. The method for evaluating the cement bond as set forth in claim 6 wherein the step to derive the impact and rebound signals further includes the steps of digitizing the motion signal to generate samples thereof at known time intervals;

storing the samples;

scanning the samples to select the sample representative of the start of impact of the element on the casing; and selecting as the impact signal a sample bearing a known time interval relationship relative to the sample representative of the start of impact of the element on the casing.

9. The method for evaluating the cement bond as set forth in claim 6 wherein the step to derive the impact and rebound signals further includes the steps of delaying the motion signal by a known interval;

detecting in the undelayed motion signal when it represents a start of impact of the element on the casing; and sampling the delayed motion signal a predetermined time after said start of impact of the element on the casing as the impact velocity of the element just prior to said impact.

10. The method for evaluating the cement bond as claimed in claim 3 and further comprising the step of applying an impulse to the element to bounce it off another casing surface segment, which is generally radially opposite said one segment, said latter impulse terminating before the element contacts said other inner casing surface segment, with said measuring step further comprising measuring the velocity of the element just prior to and after bouncing off the other inner casing surface segment.

11. An apparatus for evaluating the cement bond behind a casing cemented in a borehole, comprising an element positioned to bounce off an inner surface of the casing;

means for applying to said element an impulse advancing said element to one segment of said inner casing surface with said impulse being of a duration less than the time needed for the element to contact said inner casing surface; and means for producing a motion signal representative of the motion of the element prior to and after rebounding off said inner casing surface.

12. The apparatus for evaluating the cement bond as set forth in claim 11 and further including means responsive to said motion signal for measuring the impact and rebound velocity of the element at times just prior to and after contact of the element with said inner casing surface.

13. The apparatus for evaluating the cement bond as set forth in claim 12 and further including means for comparing impact and rebound velocities of the element as a characterization of the quality of the cement bond behind the casing.

14. The apparatus for evaluating the cement bond as set forth in claim 13 wherein said comparing means includes means for forming a ratio between said velocities as a characterization of the quality of the cement bond behind the casing.

15. The apparatus for evaluating the quality of the cement bond as set forth in claim 11 and further including means for applying an impulse to the element to drive it to another inner casing surface segment which is generally diametrally opposite said one segment, said latter impulse terminating before the element contacts said other inner casing surface segment.

16. The apparatus for evaluating the cement bond as set forth in claim 11 and further including means responsive to said motion signal for measuring the impact and rebound times of the element as represented by the times just prior to and after contact of the element with said inner casing surface.

17. The apparatus for evaluating the cement bond as set forth in claim 16 and further including means for comparing the measured impact and rebound times of the element as a characterization of the quality of the cement bond behind the casing at the segment of the casing impacted by the element.

18. The apparatus for evaluating the cement bond as set forth in claim 17 wherein said comparing means includes means for forming a difference between said times and a characterization of the quality of said cement bond behind the casing at the segment of the casing impacted by said element.

19. The apparatus for evaluating the cement bond as set forth in claim 11 and further including means responsive to said motion signal for measuring the times just prior to and just after contact of the element with said inner casing and the corresponding impact and rebound velocity of the element at these times;

means for comparing the measured times and velocities respectively as characterizations of the quality of the cement bond at the segment of the casing impact by said element; and means for recording at least one of said characterizations as a function of the location of the segment of the casing impacted by said element.

* * * * *